(12) United States Patent
Honsberg-Riedl et al.

(10) Patent No.: US 7,884,554 B2
(45) Date of Patent: Feb. 8, 2011

(54) IGNITION CIRCUIT FOR IGNITING A DISCHARGE LAMP AND METHOD FOR IGNITING THE DISCHARGE LAMP

(75) Inventors: Martin Honsberg-Riedl, Teisendorf (DE); Burkhard Ulrich, Rosenfeld (DE); Alwin Veser, Hallbergmoos (DE)

(73) Assignee: OSRAM Gesellschaft mit beschraenkter Haftung, Munich (DE)

( * ) Notice: Subject to any disclaimer, the term of this patent is extended or adjusted under 35 U.S.C. 154(b) by 547 days.

(21) Appl. No.: 11/989,303

(22) PCT Filed: Jul. 27, 2006

(86) PCT No.: PCT/EP2006/007469

§ 371 (c)(1),
(2), (4) Date: Jan. 24, 2008

(87) PCT Pub. No.: WO2007/087836

PCT Pub. Date: Aug. 9, 2007

(65) Prior Publication Data

US 2009/0153071 A1 Jun. 18, 2009

(30) Foreign Application Priority Data

Jul. 29, 2005 (DE) .................. 10 2005 035 745

(51) Int. Cl.
*H05B 37/00* (2006.01)
(52) U.S. Cl. .............. 315/219; 315/223; 315/224
(58) Field of Classification Search ............. 315/209 R, 315/224, 219, 223, 221, 220, 222, DIG. 5, 315/DIG. 7
See application file for complete search history.

(56) References Cited

U.S. PATENT DOCUMENTS 4,461,982 A * 7/1984 Fahnrich ................. 315/290

(Continued)

FOREIGN PATENT DOCUMENTS

DE 4430397 A1 8/1994

(Continued)

OTHER PUBLICATIONS

Pousset T et al., Electronic Ballast for High-Pressure Mercury Lamps., Industry Applications Conferece, 1996, Thirty-First IAS Annual Meeting, IAS '96., Conference Record of the 1996 IEEE San Diego, CA, USA Oct. 6-10, 1996, New York, NY, USA, IEEE, US, vol. 4, Oct. 6, 1996, pp. ISBN: 0-7803-3544-9, Figure 1, Abstract.

(Continued)

*Primary Examiner*—David Hung Vu

(57) ABSTRACT

A starting circuit arrangement for starting at least one discharge lamp by applying an electrical starting voltage pulse to the discharge lamp, the starting circuit arrangement has: at least one source circuit arrangement for providing an electrical primary voltage pulse, at least one starting circuit for providing the starting voltage pulse, and at least one inductive coupling element for inductively coupling-in the primary voltage pulse into the starting circuit for the purpose of generating the starting voltage pulse. The inductive coupling element has a transformation ratio for a voltage transformation which is selected from the range of from 1/25 to 1/400. A method for starting a discharge lamp by applying a starting voltage pulse using the starting circuit arrangement is also disclosed.

20 Claims, 3 Drawing Sheets

U.S. PATENT DOCUMENTS

| | | | |
|---|---|---|---|
| 5,367,227 A | * | 11/1994 | Gademann et al. .......... 315/290 |
| 5,677,601 A | | 10/1997 | Zuchtriegel |
| 2002/0047609 A1 | | 4/2002 | Weng |

FOREIGN PATENT DOCUMENTS

| | | |
|---|---|---|
| EP | 0 903 967 | 3/1999 |
| EP | 0 987 928 | 3/2000 |
| FR | 2 693 074 | 12/1999 |
| JP | 7240293 A | 9/1995 |
| JP | 8078172 A | 3/1996 |
| JP | 11265796 A | 9/1999 |
| WO | WO 96/27278 | 9/1996 |

OTHER PUBLICATIONS

English language abstract for JP 07240293.

German translation of the Japanese Office Action dated Aug. 16, 2010.

* cited by examiner

IGNITION CIRCUIT FOR IGNITING A DISCHARGE LAMP AND METHOD FOR IGNITING THE DISCHARGE LAMP

The invention relates to a starting circuit arrangement for starting at least one discharge lamp by applying an electrical starting voltage pulse to the discharge lamp, the starting circuit arrangement having the following features: at least one source circuit arrangement for providing an electrical primary voltage pulse, at least one starting circuit for providing the starting voltage pulse, and at least one inductive coupling element for inductively coupling-in the primary voltage pulse into the starting circuit for the purpose of generating the starting voltage pulse. In addition to the starting circuit arrangement, a method for starting a discharge lamp using the starting circuit arrangement is specified.

A starting circuit arrangement of the type mentioned is in each case known from EP 0 903 967 A1 and EP 0 987 928 A1. When the discharge lamp is started, a gas in a lamp arcing chamber of the discharge lamp is ionized. The gas consists of, for example, mercury vapor. An electrically conductive plasma results. This plasma causes the discharge lamp to first illuminate. In order to maintain this illumination and rapid heating of inner electrodes of the lamp arcing chamber, the discharge lamp is driven, for example, by a sinusoidal alternating current (starting transfer current). A frequency of this alternating current is, for example, 200 kHz. A starting transfer voltage of the discharge lamp at room temperature is, for example, from 150 V to 500 V. After a starting transfer time in the seconds range (below one second to a few seconds), the actual operating current can be impressed. The operating current is sinusoidal or it has a square-wave form. An operating voltage required for this purpose is, for example, from 15 V to 225 V. From this phase on (after 1 min to 4 min), the discharge lamp enters the desired, severely heated operating state with a high internal pressure in the lamp arcing chamber, a very high luminous efficacy and a broadband emission spectrum.

For starting purposes, the inner electrodes of a lamp arcing chamber of the discharge lamp are driven by the starting voltage pulse. An electrical flashover results which leads to ionization of the gas. The starting voltage pulse is a set of a large number of voltage pulses (voltage pulse train). A pulse repetition rate of the voltage pulses within a voltage pulse train is from 1 MHz to 10 MHz. In order that the discharge lamp is started, starting voltage pulses having a peak voltage in the kV range are required. The starting voltage pulses are therefore high-voltage pulse trains in the radiofrequency range (high-voltage RF burst). The starting transfer voltage is superimposed with these high-voltage pulse trains during the starting process. The starting circuit arrangement is designed such that superimposition and therefore starting of the discharge lamp occurs at a maximum starting transfer voltage.

The known starting circuit arrangement essentially comprises a source circuit arrangement, a starting circuit in the form of a resonant circuit (starting resonant circuit, secondary resonant circuit) and an inductive coupling element in the form of a starting transformer. The discharge lamp is connected electrically in parallel with the starting resonant circuit. In the source circuit arrangement, the primary voltage pulse is generated. With the aid of the starting transformer, the primary voltage pulse is coupled-in into the starting resonant circuit. The starting voltage pulse is produced in the starting resonant circuit. This results in starting of the discharge lamp. The components of the starting circuit arrangement, in particular the starting transformer of the inductive coupling element, are designed such that a magnification factor Q of the starting resonant circuit results which is as high as possible. The magnification factor Q is over 100.

A starting circuit arrangement for starting a discharge lamp is implemented, for example, in a so-called electronic ballast (EB). The EB converts electrical energy from an available system voltage such that the discharge lamp can be operated in its optimum voltage, current and frequency range. For example, the discharge lamp is a high-pressure lamp or an ultra-high-pressure lamp, which are used as video and projection lamps (VIP lamps).

At a relatively low lamp temperature (for example, room temperature, approximately 20° C.), a peak voltage for the starting voltage pulse of several hundred to a few thousand volts is sufficient for initiating the electrical flashover between the inner electrodes of the lamp. The higher the lamp temperature, the higher the peak voltage required for starting the high-pressure or ultra-high-pressure lamp. In the case of a VIP lamp, operating temperatures of from 950° C. to 1050° C. generally occur. The starting voltage required for the electrical flashover between the inner electrodes is extremely high at these temperatures, since the gas in the lamp arcing chamber has a severely electrically insulating effect owing to a prevailing gas pressure. This results in the VIP lamp needing to be cooled before it can be started again. The temperature of the arcing chamber needs to be reduced to approximately 500° C. in the case of contemporary ballasts. Starting from a burner operating temperature of the VIP lamp of approximately 1000° C., cooling to 500° C. lasts for approximately 30 seconds. Within the cooling time of 30 seconds, restarting (hot restarting) of the VIP lamp fails without any additional measures.

One object of the present invention is to specify an electrical starting circuit arrangement which is suitable for starting a discharge lamp even within the cooling time of the lamp.

In order to solve the object, the invention specifies a starting circuit arrangement for starting at least one discharge lamp by applying an electrical starting voltage pulse to the discharge lamp, the starting circuit arrangement having the following features: at least one source circuit arrangement for providing an electrical primary voltage pulse, at least one starting circuit for providing the starting voltage pulse, and at least one inductive coupling element for inductively coupling-in the primary voltage pulse into the starting circuit for the purpose of generating the starting voltage pulse. The starting circuit arrangement is characterized by the fact that the inductive coupling element has a transformation ratio for a voltage transformation which is selected from the range of from 1/25 to 1/400, inclusive. The transformation ratio is preferably selected from the range of from 1/40 to 1/200, inclusive, and in particular from the range of from 1/40 to 1/70, inclusive.

In order to solve the object, the invention also specifies a method for starting a discharge lamp by applying a starting voltage pulse using the starting circuit arrangement as claimed in one of the preceding claims, having the following method steps: a) forming the starting resonant circuit with a discharge lamp connected in parallel, and b) generating the starting voltage pulse in the starting resonant circuit.

The discharge lamp or the inner electrodes of the discharge lamp are connected to the starting resonant circuit, together with further components. The starting circuit has all of the reactive components required. Owing to the high transformation ratio and the resonant voltage spike, which occurs either in the starting circuit or in the coupling element, a radiofrequency starting pulse with a very high peak voltage is generated in the starting circuit. A starting voltage pulse with a peak voltage of from 10 kV to 50 kV, inclusive, and in particular with a peak voltage of from 15 kV to 25 kV, inclusive, is preferably generated.

A radiofrequency voltage pulse with a pulse repetition rate in the MHz range is generated. In one preferred refinement, a starting voltage pulse with a pulse repetition rate of from 0.5 MHz to 30 MHz, inclusive, and in particular of from 0.9 MHz to 10 MHz, inclusive, is generated. Particularly good results have been achieved, for example, at a pulse repetition rate of 1.5 MHz.

At this pulse repetition rate and at the high voltages, the starting pulse duration of the starting voltage pulse can be maintained for a short period of time. The starting pulse duration is below 50 µs. In one particular refinement, a starting voltage pulse having a starting pulse duration from the range of from 5 µs to 30 µs, inclusive, is generated. In particular, starting pulse durations of below 20 µs are possible. These relatively short starting voltage pulses are sufficient for making it possible to start the discharge lamp even at high temperatures of the discharge lamp owing to the high transformation ratio.

Frequent repeat starts make it possible to increase the starting probability. In accordance with one further refinement, the starting voltage pulse is therefore generated at a repetition rate from the range of from 50 Hz to 10 kHz, inclusive, and in particular from the range of from 100 Hz to 1 kHz, inclusive. At the repetition rate, a starting voltage pulse is coupled-in into the starting circuit. At a relatively high repetition rate, for example, 1 kHz, the probability of starting being successful within a specific time interval is increased.

The inductive coupling element has at least one starting transformer. The starting transformer has a primary inductance with at least one primary winding and a secondary inductance with at least one secondary winding. The secondary inductance of the starting transformer is part of the starting circuit. The starting circuit may be in the form of a starting resonant circuit. With the aid of the starting transformer, the primary voltage pulse formed in the source circuit arrangement is coupled-in into the starting resonant circuit. For this purpose, the starting transformer is preferably an RFHV transformer having a ferromagnetic core (for example, ferrite or ferrous powder core). The RFHV transformer is designed such that it alone provides the high voltage transformation. The RFHV transformer is therefore, for example, a transformer having an output voltage of 25 kV. Using a starting transformer with such a design, a markedly poorer magnification factor of the starting resonant circuit is possible. The starting resonant circuit has a magnification factor Q of below 100.

The inductive coupling element may have merely the correspondingly designed starting transformer. In one particular refinement, the inductive coupling element has at least one coupling transformer. The starting transformer and the coupling transformer are electrically connected to one another such that, together, they form the inductive coupling element. In one particular refinement, the starting transformer and the coupling transformer are connected in series, for this purpose. The primary inductance of the coupling transformer may be part of the source circuit arrangement. The secondary inductance of the coupling capacitor and the primary inductance of the starting transformer are electrically connected. The secondary inductance of the starting transformer is in turn part of the starting resonant circuit.

The coupling transformer is used for voltage matching. This means that the high transformation ratio of the inductive coupling element is provided by the starting transformer together with the coupling transformer. The transformation ratio does not originate from the starting transformer alone. The starting transformer therefore makes a lesser contribution. This makes it possible for the secondary inductance and therefore the secondary winding of the starting transformer to be kept small. This is associated with the following particular advantages: the nonreactive resistance of the secondary winding is reduced by a low number of turns and therefore by a shorter wire length. The nonreactive resistance also has the operating current of the discharge lamp flowing through it and therefore leads to a permanent power loss which needs to be avoided. Furthermore, the coupling capacitor results in further decoupling of the starting resonant circuit and the source circuit arrangement. A resonant voltage spike required for forming the starting voltage pulse is therefore facilitated in the starting resonant circuit.

With the explained combination of the starting transformer and the coupling transformer, it is possible, with a favorable design of the further components in the starting circuit, for starting voltage pulses to be achieved with a peak voltage of over 30 kV. In other words, this is the voltage which, calculated from the positive maximum to the negative maximum, has 60 kVpp (with the assumption that, in the present case, the voltage is approximately sinusoidal).

In one particular refinement, the inductive coupling element has at least one coupling resonant circuit. With the coupling resonant circuit, a coupling transformer may be superfluous. However, a coupling transformer is preferably provided, and the coupling resonant circuit electrically connects the starting transformer and the coupling transformer to one another. The coupling resonant circuit is also referred to as a tank resonant circuit. It is inserted between the coupling transformer and the starting transformer such that it takes over the resonance of the secondary winding of the starting transformer. A resonant voltage spike, triggered by the primary voltage pulse of the source circuit arrangement, occurs in the coupling resonant circuit. On the other hand, the starting circuit is not in the form of a starting resonant circuit. In this case, no resonant voltage spike occurs. Only one starting voltage pulse is generated at the inner electrodes of the discharge lamp via the starting transformer. In this particular refinement, too, the starting transformer does not provide the transformation ratio for the entire inductive coupling element alone. The level of the transformation ratio depends to a very great extent on the design of the tank circuit, which has a self-transforming effect either owing to suitable capacitive or inductive tapping or, in addition, owing to a coupling transformer being connected upstream, as a result of its contribution. For example, the tank resonant circuit develops a voltage of from 2 kV to 10 kV. A moderate transformation for the starting transformer is therefore possible. It is possible to dispense with the coupling transformer depending on the type of source circuit arrangement.

The source circuit arrangement has a suitable radiofrequency switching element. The radiofrequency switching element has one or more radiofrequency switching transistors. The radiofrequency switching transistor is a (power) MOS transistor and, in particular a CoolMOS® transistor or powerMESH™ transistor or an FDmesh™ transistor or a silicon carbide FET transistor.

The source circuit arrangement provides a high power for the pulse duration. The source circuit arrangement is designed such that an average primary power is between 300 W and 2 kW. This results in a radiofrequency switching transistor used for switching purposes carrying current pulses having a peak current of between 10 A and 100 A. In this case, provision is made for an efficiency to be sufficiently high. The cost of a radiofrequency switching transistor depends to a very considerable extent on its current-carrying capacity. The higher the efficiency of the source circuit arrangement, the lower current-carrying capacity can be selected for the radiofrequency switching transistor(s).

In one particular refinement, the source circuit arrangement for providing the primary voltage pulse has a radiofrequency switching element with switching load relief. This in general means that, at the time at which the switching element is switched on, the applied voltage and the carried current are equal to or close to zero. In this manner, it is possible to avoid a power loss peak which normally occurs during the switching operation. A source circuit arrangement having a particularly high efficiency results. One further important advantage of the switching load relief is represented by the avoidance of severe electromagnetic interference components (EMC problem) at and far above the switching frequency.

The source circuit arrangement preferably has a topology which is selected from the group consisting of class E, class D and class DE. Class E and class DE are characterized by particularly effective switching load relief. Owing to the high switching load relief, an electrolyte capacitor, which is generally required as the supply buffer store for the source circuit arrangement, can be kept small. Furthermore, only a radiofrequency switching transistor which only needs a limited current-carrying capacity owing to the increased efficiency is required for this switching stage. A relatively inexpensive starting circuit arrangement therefore results. One further advantage consists in the fact that an output voltage of the switching stage, without any further matching, almost linearly follows a DC voltage used to supply the switching stage. This makes it possible to regulate the radiofrequency voltage via an upstream voltage supply of the source circuit arrangement.

There are two types of class E: a parallel circuit or a series circuit may be connected to the drain or collector terminal of the transistor. The second solution is characterized by the fact that it can be operated at very low supply voltages. It is therefore possible to use a heavy-duty transistor having a relatively low blocking capacity.

Very effective switching load relief is also achieved by a radiofrequency switching stage of the class DE. This class is based on a half bridge comprising two switching transistors. The switching transistors used require a markedly lower dielectric strength than the switching transistor which is used in class E.

The starting circuit arrangement is used in particular in EBs for high-pressure discharge lamps and for ultra-high-pressure discharge lamps, as are used in video and projection technology. In the case of a high-pressure discharge lamp, pressures of from 2 bar to 20 bar occur in the lamp arcing chamber. In the case of ultra-high-pressure lamps, the pressures fluctuate in the range from 100 bar to 200 bar. The intention here is to achieve an emission spectrum which is as broad as possible. A power for the VIP lamps is between 100 W and 300 W, for example 120 W. Higher and lower powers are also conceivable. Using the starting circuit it is possible to start such discharge lamps even in the hot state during operation at temperatures of over 500° C. up to 1000° C.

In summary, the following essential advantages result with the invention:

The starting circuit arrangement makes it possible for a discharge lamp to be restarted even at high temperatures of over 500° C. Once the illumination of the discharge lamp has been interrupted, it is not necessary for there to be cooling for restarting. There is no delay in starting.

With the invention it is possible to dispense with an auxiliary starting electrode, which is often used for maintaining the delay in starting which is conventional nowadays.

The invention will be explained in more detail below with reference to a plurality of exemplary embodiments and the associated figures, in which.

Figure 1:
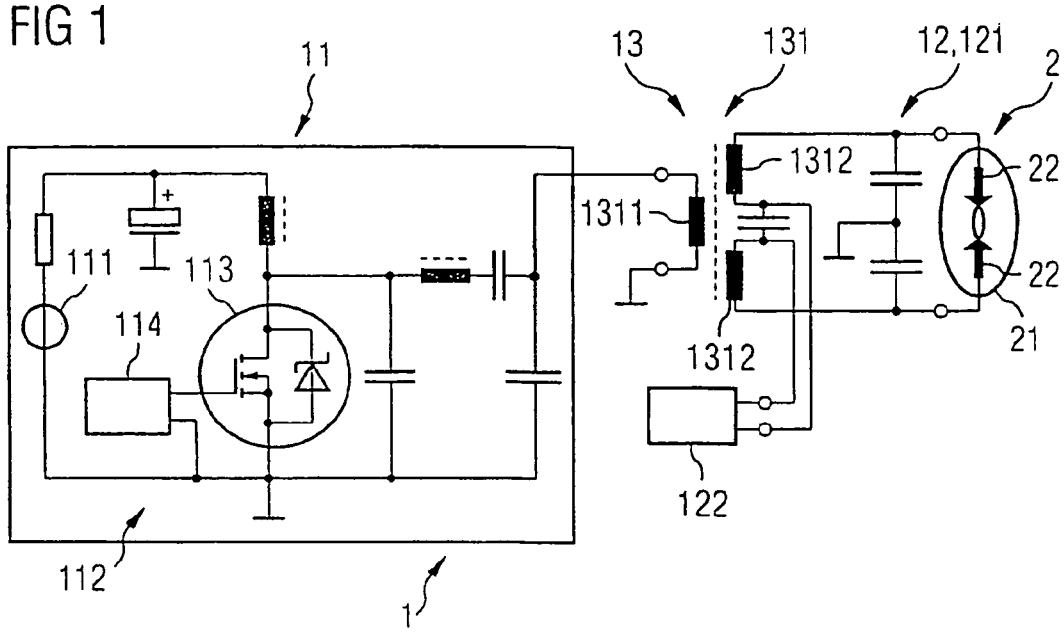
FIGS. 1, 2, 3A and 3B show circuit diagrams of various exemplary embodiments of the starting circuit arrangement.

The starting circuit arrangement 1 for starting a discharge lamp 2 by applying an electrical starting voltage pulse is implemented in an EB for a high-pressure discharge lamp 2. The high-pressure discharge lamp 2 is a VIP discharge lamp having a power of 120 W. In alternative embodiments to this, the VIP discharge lamp has a power of 100 W or 300 W.

The essential components of the starting circuit arrangement 1 are the source circuit arrangement 11 for providing the primary voltage pulse, the starting circuit 12 for providing the starting voltage pulse and the inductive coupling element 13 for inductively coupling-in the primary voltage pulse into the starting circuit 12. The starting voltage pulse results from the primary voltage pulse being coupled-in into the starting circuit 12.

The inner electrodes 22 of the high-pressure discharge lamp 2 which are arranged in the lamp arcing chamber 21 are components in the starting circuit 12. The starting voltage pulse generated in the starting circuit 12 leads to an electrical flashover between the inner electrodes 22. The gas in the interior of the lamp arcing chamber 21 is ionized. The heating plasma for the starting transfer is formed.

In order to maintain the heating plasma, the high-pressure discharge lamp 2 is driven, via the voltage supply unit 122, with a sinusoidal-like starting transfer voltage. The voltage supply unit 122, which is integrated in the EB, makes available a sinusoidal-like starting transfer voltage of between 150 V and 500 V in the 100 kHz range.

The source circuit arrangement 11 is supplied with a suitable electrical DC voltage via the voltage supply unit 111. The source circuit arrangement 11 has a radiofrequency switching element 112. The radiofrequency switching element 112 has switching load relief. This means that, at the time at which it is switched on, the applied voltage and the carried current is zero or close to zero. Components of the radiofrequency switching element 112 are at least one radiofrequency switching transistor 113 and at least one RF driver circuit 114. The radiofrequency switching transistor 113 is driven by the RF driver circuit 114. The radiofrequency switching transistor 113 is a CoolMOS® transistor. In alternative refinements to this, a powerMESH™ transistor, an FDmesh™ transistor or a silicon carbide FET transistor are used. The RF driver circuit 114 provides a radiofrequency switching signal for the radiofrequency switching transistor 113, which signal is matched to the pulse repetition rate of the starting voltage pulse to be achieved. This means that a primary voltage pulse is generated in the source circuit arrangement 11 and has an identical or very similar pulse repetition rate to that of the starting voltage pulse in the starting circuit 12.

With the aid of the starting circuit arrangement 1, a radiofrequency starting voltage pulse is generated for starting the discharge lamp 2. A pulse repetition rate of the starting voltage pulse, in a first embodiment, is approximately 1.5 MHz. In a further embodiment, the pulse repetition rate is 4 MHz. The peak voltage of the starting voltage pulse is 22 kV. This corresponds to 44 kVpp. In a further embodiment, the peak voltage of the starting voltage pulse is 30 kV (60 kVpp). The starting pulse duration is 20 µs. In a further embodiment, the starting pulse duration is 5 µs.

The inductive coupling element 13 has a transformation ratio for the voltage transformation of approximately 1/60. This high transformation ratio makes it possible to achieve the radiofrequency voltage pulses with the high peak voltage. Owing to the high peak voltage, it is possible to start the VIP high-pressure discharge lamp at high burner surface temperatures of over 500° C. It is not necessary to wait for the cooling phase to elapse for successful restarting of the discharge lamp.

In order to achieve the high transformation ratio, three examples are specified below:

EXAMPLE 1

The associated circuit diagram is reproduced in FIG. 1. The inductive coupling element 13 merely comprises a starting transformer 131. The starting transformer 131 produces the high transformation ratio on its own. A primary inductance 1311 of the starting transformer 131 is a component of the source circuit arrangement 11. The secondary inductance 1312 of the starting transformer 131 is a component of the starting circuit 12, which is in the form of a starting resonant circuit 121. The primary voltage pulse is coupled-in into the starting resonant circuit 121 via the primary inductance 121 and the secondary inductance 1312 of the starting transformer 131.

The starting transformer 131 is an RFHV transformer having a ferromagnetic core and corresponding numbers of turns of the primary inductance 1311 and the secondary inductance 1312. The starting resonant circuit 121 has a magnification factor Q of far below 100.

The secondary inductance 1312 comprises two virtually identical inductance elements having the same winding sense. These inductance elements are combined with further components to form a virtually symmetrical starting resonant circuit 121. This makes it possible for the operating voltage and the starting transfer voltage to be fed without any influence by the high-voltage pulses for starting.

The radiofrequency switching element 112 of the source circuit arrangement 11 has a class E radiofrequency switching stage (series topology).

EXAMPLE 2

Figure 2:
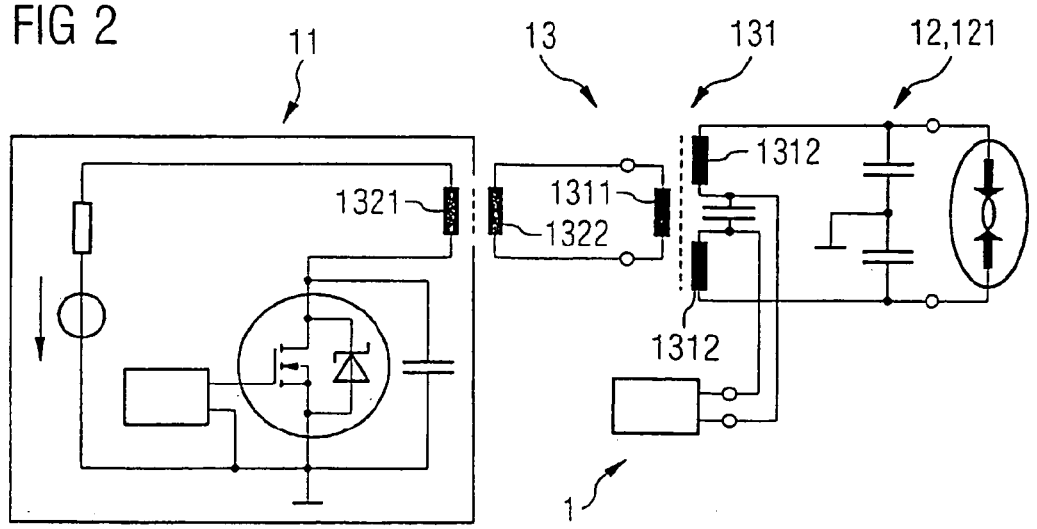

The corresponding circuit diagram can be seen in FIG. 2. In contrast to example 1, the inductive coupling element 13 has a coupling transformer 132 in addition to the starting transformer 131. The high transformation ratio is achieved by the starting transformer 131 being coupled to the coupling transformer 132. For this purpose, a primary inductance 1321 of the coupling transformer 132 is a component in the source circuit arrangement 11. The primary voltage pulse is coupled-in into the starting resonant circuit 121 indirectly via the secondary inductance 1322 of the coupling transformer 132 and the primary inductance 1311 of the starting transformer 131. A corresponding refinement of the coupling transformer 132 achieves a part-transformation ratio. The part-transformation ratio of the starting transformer 131 can therefore be reduced. The high transformation ratio of the entire inductive coupling element 13 is maintained.

The radiofrequency switching element 112 of the source circuit arrangement 11 likewise has a class E radiofrequency switching stage, but with a parallel topology.

EXAMPLE 3

Figure 3A:
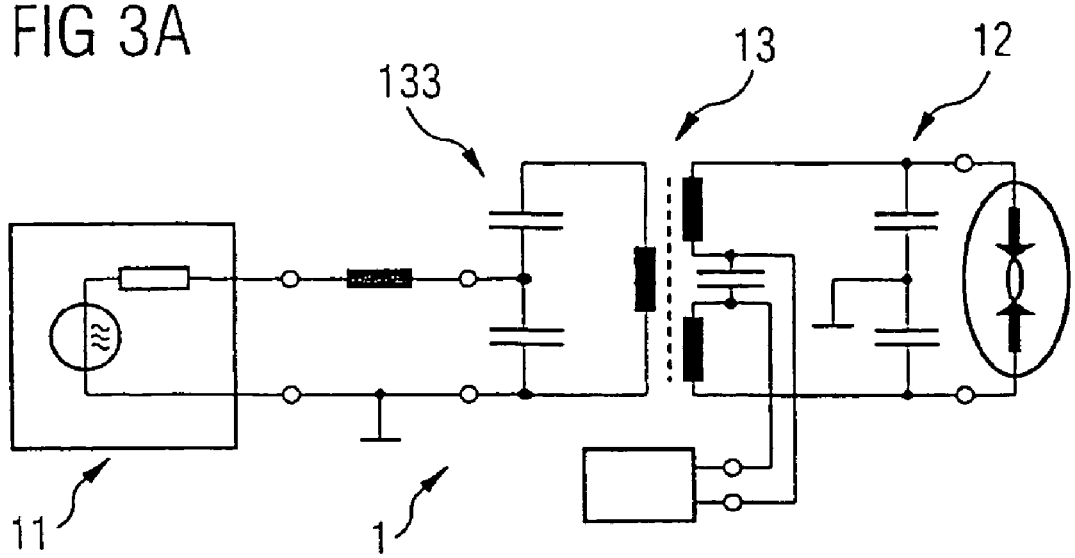
Figure 3B:
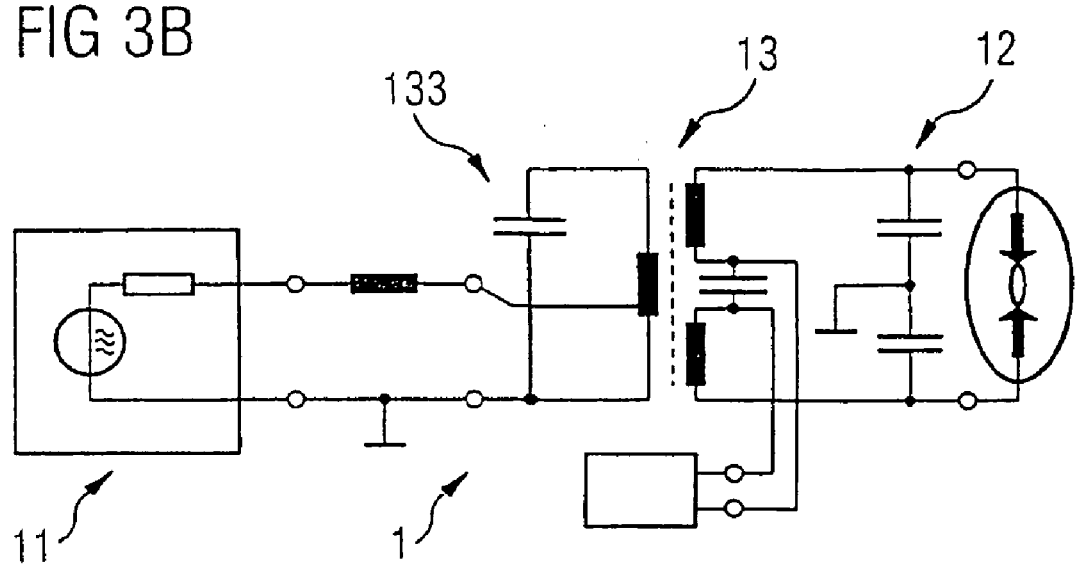

The associated circuit diagram is shown by FIGS. 3A and 3B. The starting circuit 12 is not in the form of a starting resonant circuit. This means that the starting circuit 12, apart from parasitic elements, cannot be caused to oscillate in the frequency range of the starting voltage pulse.

In order to induce the starting voltage pulse in the starting circuit 12, the inductive coupling element 13 has a tank resonant circuit (coupling resonant circuit) 133. The tank resonant circuit 133 has a capacitive divider (FIG. 3A). As an alternative to this, the tank resonant circuit 133 is in the form of a tank resonant circuit having a tapped coil (tapped tank resonant circuit, FIG. 3B). This tank resonant circuit 133, in a development of the coupling element 13 in accordance with the preceding example, is connected between the coupling transformer 132 and the starting transformer 131. The primary inductance 1311 of the starting transformer is a component in the tank resonant circuit 133. Here, too, a part-transformation ratio is taken over by the tank resonant circuit. The starting transformer 131 can therefore manage with a smaller transformation ratio.

Figure 4:
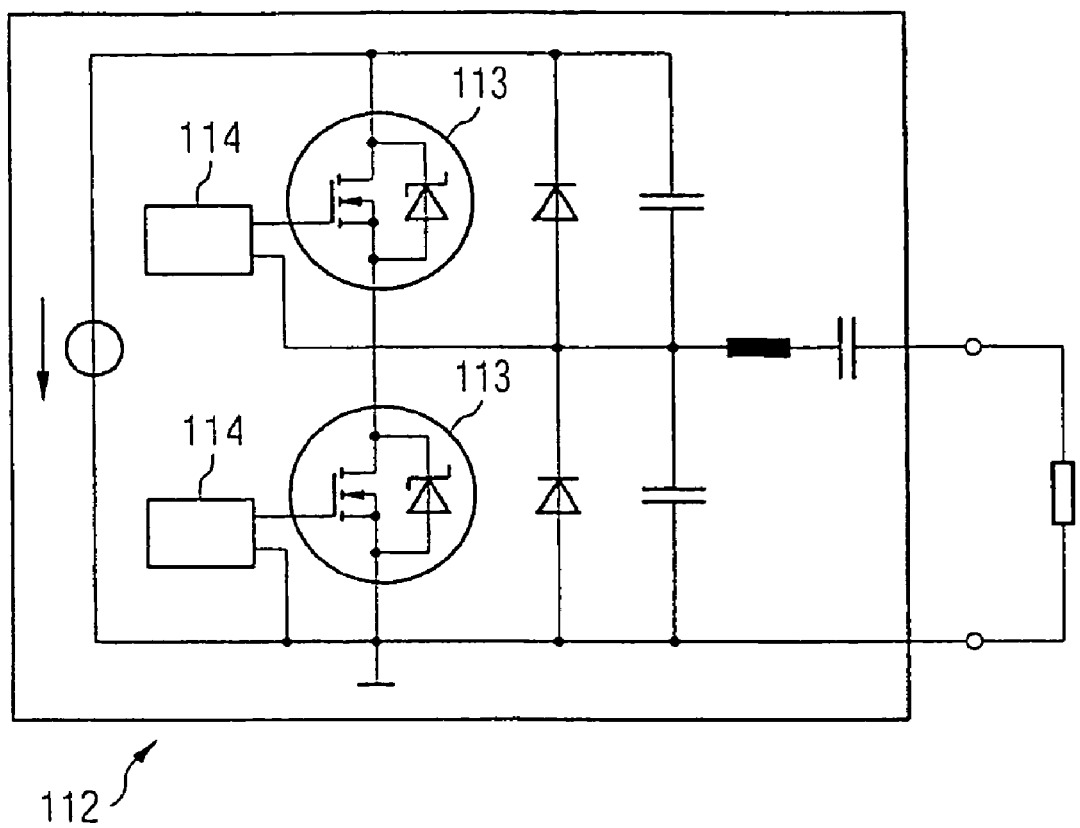
FIG. 4 shows the circuit diagram of a radiofrequency switching stage of the class DE.

In addition to the examples described, there is also a large number of embodiments which result from corresponding refinements of the source circuit arrangement 11, the starting circuit 12 or the coupling element 13 and its components. For example, the secondary inductance 1312 of the starting transformer 131 has one part, in accordance with an embodiment which is not illustrated. More than two components are likewise conceivable. In a further embodiment, a radiofrequency switching element 112 with a DE class switching stage is used for the source circuit arrangement 11 as an alternative to the radiofrequency switching element 112 with the E class switching stage. A DE switching stage with a series circuit topology is shown in FIG. 4. The radiofrequency switching stage of this class has two radiofrequency switching transistors 113. Each of the radiofrequency switching transistors can be driven by a dedicated RF driver circuit 114.

The invention claimed is:

1. A starting circuit arrangement (1) for starting at least one discharge lamp (2) by applying an electrical starting voltage pulse to the discharge lamp, the starting circuit arrangement having the following features:
    at least one source circuit arrangement (11) for providing an electrical primary voltage pulse,
    at least one starting circuit (12) for providing the starting voltage pulse, and
    at least one inductive coupling element (13) for inductively coupling-in the primary voltage pulse into the starting circuit for the purpose of generating the starting voltage pulse,
    characterized in that
    the inductive coupling element has a transformation ratio for a voltage transformation which is selected from the range of from 1/25 to 1/400.

2. The starting circuit arrangement as claimed in claim 1, the transformation ratio being selected from the range of from 1/40 to 1/200 and in particular from the range of from 1/40 to 1/70.

3. The starting circuit arrangement as claimed in claim 1, the inductive coupling element having at least one starting transformer (131).

4. The starting circuit arrangement as claimed in claim 3, the starting transformer being an RFHV transformer having a ferromagnetic core.

5. The starting circuit arrangement as claimed in claim 1, the starting circuit having a starting resonant circuit having a magnification factor of below 100.

6. The starting circuit arrangement as claimed in claim 1, the inductive coupling element having at least one coupling transformer (132).

7. The starting circuit arrangement as claimed in claim 1, the inductive coupling element having at least one coupling resonant circuit (133).

8. The starting circuit arrangement as claimed in claim 7, the coupling resonant circuit (133) electrically connecting the starting transformer and the coupling transformer to one another.

9. The starting circuit arrangement as claimed in claim 1, the source circuit arrangement for generating the primary voltage pulse having a radiofrequency switching element (112) with switching load relief.

10. The starting circuit arrangement as claimed in claim 1, the source circuit arrangement having a topology which is selected from the group consisting of class E, class D and class DE.

11. A method for starting a discharge lamp by applying a starting voltage pulse using the starting circuit arrangement as claimed in claim 1, having the following method steps:
 a) forming the starting resonant circuit with a discharge lamp connected in parallel, and
 b) generating the starting voltage pulse in the starting resonant circuit.

12. The method as claimed in claim 11, a starting voltage pulse having a peak voltage of from 10 kV to 50 kV and in particular having a peak voltage of from 15 kV to 25 kV being generated.

13. The method as claimed in claim 11, a starting voltage pulse having a pulse repetition rate of from 0.5 MHz to 30 MHz and in particular of from 0.9 MHz to 10 MHz being generated.

14. The method as claimed in claim 11, a starting voltage pulse having a starting pulse duration from the range of from 5 µs to 30 µs, inclusive, being generated.

15. The method as claimed in claim 11, the generation of the starting voltage pulse being repeated at a repetition rate from the range of from 50 Hz to 10 kHz and in particular from the range of from 100 Hz to 1 kHz.

16. The method as claimed in claim 11, starting taking place at a lamp temperature of the discharge lamp of over 500° C.

17. The method as claimed in claim 11, a high-pressure discharge lamp and, in particular, an ultra-high-pressure discharge lamp being used as the discharge lamp.

18. The starting circuit arrangement as claimed in claim 2, the inductive coupling element having at least one starting transformer (131).

19. The starting circuit arrangement as claimed in claim 18, the starting transformer being an RFHV transformer having a ferromagnetic core.

20. The method as claimed in claim 12, a starting voltage pulse having a pulse repetition rate of from 0.5 MHz to 30 MHz and in particular of from 0.9 MHz to 10 MHz being generated.

* * * * *